United States Patent [19]

Malcolme-Lawes et al.

[11] 4,427,892
[45] Jan. 24, 1984

[54] DETECTION AND DETERMINATION OF SPECIES BY FLUORESCENCE MEASUREMENTS

[75] Inventors: David J. Malcolme-Lawes, Loughborough; Lawrence A. Gifford, Bury, both of England

[73] Assignee: National Research Development Corporation, London, England

[21] Appl. No.: 237,140

[22] PCT Filed: Jun. 6, 1980

[86] PCT No.: PCT/GB80/00098
§ 371 Date: Feb. 9, 1981
§ 102(e) Date: Feb. 9, 1981

[87] PCT Pub. No.: WO80/02746
PCT Pub. Date: Dec. 11, 1980

[30] Foreign Application Priority Data

Jun. 7, 1979 [GB] United Kingdom ............... 7919852

[51] Int. Cl.$^3$ .................. G01N 23/00; G21K 5/00
[52] U.S. Cl. ................... 250/458.1; 250/308; 250/459.1
[58] Field of Search ............... 250/358.1, 359.1, 458.1, 250/459.1, 308; 378/47; 73/23.1; 422/70, 71, 89; 436/172

[56] References Cited

U.S. PATENT DOCUMENTS 3,751,661 8/1973 Packer et al. ................ 378/47
4,125,769 11/1978 Marten et al. ................ 378/47

FOREIGN PATENT DOCUMENTS 1103562 2/1968 United Kingdom .
1158871 7/1969 United Kingdom .
1173287 12/1969 United Kingdom .
1193840 6/1970 United Kingdom .
1350523 4/1974 United Kingdom .
1456098 11/1976 United Kingdom .
1461270 1/1977 United Kingdom .

OTHER PUBLICATIONS

Jordan et al., *Specialia* 15.3.1969, pp. 335-336.

*Primary Examiner*—Janice A. Howell
*Attorney, Agent, or Firm*—Oblon, Fisher, Spivak, McClelland & Maier

[57] ABSTRACT

A fluorimetric detector for use in detecting or determining a species contained in the flowing liquid eluant of a chromatographic separation, comprising: a $^{147}$Pm or $^{63}$Ni source of beta-particles; a light-sensitive detection means, spaced from the source, for detecting visible fluorescent radiation generated in the eluant by the action thereon of beta-particles and for measuring a count rate of said fluorescent radiation; and flow-causing means to cause the eluant to flow between the source and the detection means is disclosed. Also disclosed, is a method of detecting or determining a species contained in the flowing liquid eluant of a chromatographic separation, the species being either a fluorescent species or a species which quenches fluorescence.

9 Claims, 16 Drawing Figures

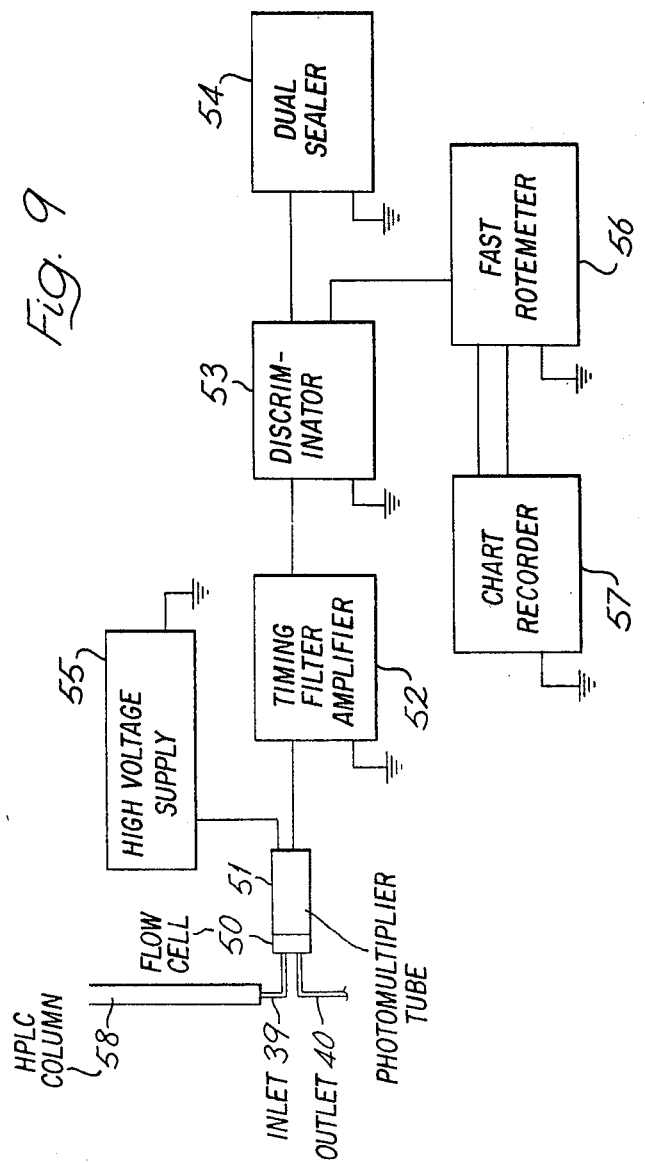

DETECTION AND DETERMINATION OF SPECIES BY FLUORESCENCE MEASUREMENTS

This invention relates to the detection and determination of species by fluorescence measurements, including detection and determination of both fluorescent species and species which cause quenching of fluorescence, and in particular to detection and determination of these species in flowing liquid systems such as liquid chromatography systems.

Liquid chromatography techniques are very widely used for separation and determination of chemical compounds contained in mixtures, and amongst the various detectors which are used to detect compounds of interest after separation, fluorescence detectors are particularly preferred in view of their high degree of sensitivity. Currently available fluorimetric detectors use visible radiation to bring about excitation of the fluorescent species which gives rise to problems of instability. A mercury line or Xenon arc lamp is usually used for exciting fluorescence but both are susceptible to variations in intensity, so that expensive power supplies or other electronic systems must be used to compensate for radiation intensity fluctuation. Furthermore, since the emitted fluorescent radiation must be detected at right angles to the incident exciting radiation, a substantial proportion of the total fluorescence is generally lost. Moreover, the use of filters and monochromators to reduce interference results in a further reduction in the proportion of the total fluorescent radiation which can be detected.

A new and improved form of fluorimetric detector has now been devised, particularly for use in liquid chromatography systems, which does not suffer from the instability of prior art visible radiation excitation fluorimetric detectors, and moreover advantageously permits detection of a greater proportion of the total fluorescence produced than prior fluorimetric detectors.

According to the present invention a fluorimetric detector comprises a radionuclide as the fluorescence excitation source.

The invention also includes a method for the detection or determination of a species by fluorescence measurements, in which liquid comprising the species to be determined is exposed to fluorescence exciting radiation from a radionuclide source and fluorescence thereby produced is monitored and compared with the fluorescence of the same liquid in the absence of the species.

The detector and method of the invention are widely applicable to the detection and determination in liquids of fluorescent species and species which cause quenching of fluorescence, generally in flowing liquid systems. For instance, the invention may be applied to the monitoring of such species in effluent, liquid product, e.g. petrochemical product, or other streams. In particular, however, the invention is applicable to fluorescence detection in liquid chromatography systems, especially high performance liquid chromatography (HPLC) systems.

The species which may be detected and determined by the present invention may be any species which are fluorescent in response, either directly or indirectly, to radionuclide radiation or cause quenching of such fluorescence, and may include any of those species which may be determined by conventional fluorescence techniques which use visible radiation to excite fluorescence. Such species include fluorescent species such as unsaturated hydrocarbons, e.g. those unsaturated hydrocarbons which may be present in a petrochemical product stream. Such species may also include species which quench fluorescence such as halogen substituted hydrocarbons, thionyl compounds and aldehydes. Generally, however, the invention may be used to detect or determine specific species such as drugs, aromatic compounds and polycyclic hydrocarbons, which it may be desired to detect in liquid chromatography systems. For example, fluorescent species which may be detected using the method and apparatus of the invention include: p-terphenyl, anthracene, fluorene, 1,6-diphenyl-1,3,5-hexatriene, 1,4-di(2-methylstyryl)benzene, biphenyl, tetraphenylbutadiene naphthalene, phenanthrene, acenaphthene, anisole, indene, benz(a)pyrene, 3-methylcholanthrene, fluoranthene, 2,5-diphenyloxazole, dibenzofuran, carbazole, indole, salicylic acid, anthranilic acid, 9-amino acridine and 1-naphthol. Similarly, for example, species which cause quenching of fluorescence and which may be detected or determined using the method and apparatus of the invention include: 1,2-dibromomethane, iodoethane, 1-bromopropane, tetrachlorethene, 1,2-dichloroethane, nitrobenzene, chlorobenzene, p-dichlorobenzene, hexachlorobenzene, 3-chlorotoluene, 4-chlorotoluene, thiophen, propanone, butan-2-one, ethanol, anisaldehyde, cinnamaldehyde, benzaldehyde and nitropropane.

It will be appreciated, of course, that when the species to be detected or determined is one which causes quenching of fluorescence, it is necessary to have some other species present to provide the background fluorescence which is quenched. This background fluorescence may be provided by any suitable fluorescent species including the solvent e.g. hexane, or fluorescent species present as impurities in the solvent. Also, it may be advantageous to dope the solvent with specific fluorescent materials e.g. anthracene or toluene, in order to increase the amount of background fluorescence, though such fluorescent dope materials are preferably such as not to interfere with the chromatographic separation.

The radionuclide source used to excite fluorescence may be any suitable radionuclide source, though it will be appreciated that the energy of the source is such that electrons produced either indirectly or directly by the radionuclide radiation have energies which are preferably less than the Cerenkov threshold for the liquid system in which the species is contained, e.g. less than about 263 keV for water. Usually, also the radionuclide source is of ralatively long half life, normally a half life of at least six months though usually longer half life e.g. a half life of at least two years, preferably at least ten years and especially at least 50 years, such that the detector does not require frequent recalibration to take account of the radioactive decay of the source.

The radionuclide source used may be such as to directly cause fluorescence. For instance, the radionuclide source may comprise a $\beta$-emitting radionuclide, such that interaction of emitted beta particles with a solution of a fluorescent species causes the fluorescent species to fluoresce. Suitable $\beta$-emitting radionuclide sources includes $^3$H, $^{14}$C, $^{35}$S, $^{147}$Pm and $^{63}$Ni, of which $^3$H or especially $^{63}$Ni and $^{147}$Pm are particularly preferred.

Alternatively the radionuclide source may cause fluorescence excitation of a fluorescent species indirectly. For instance, the radionuclide source may comprise an α-emitting or preferably a γ-emitting radionuclide source, in which case the α or γ radiation may cause fluorescent excitation of the species indirectly via direct interaction of the species with electrons ejected from other materials e.g. solvent molecules, by the radionuclide radiation. For example, a γ-emitting radionuclide may be used producing γ photons which cause photoelectronic ejection of electrons from solvent molecules, e.g. water or hexane molecules, and these electrons may interact directly with the species to cause fluorescence. Again it will be appreciated that such photo-electronically ejected electrons preferably have energies below the Cerenkov threshold for the liquid system used.

The detector of the invention may take various forms. Thus for use with flowing liquid systems, e.g. liquid chromatography systems the detector typically comprises a passageway for liquid flow together with a monitoring system for monitoring the fluorescent radiation produced. Typically the monitoring system is located outside the liquid passageway and the walls of the passageway are transparent, at least in part, to permit transmission of the fluorescent radiation to the monitoring system. The radionuclide source may be contained within the liquid passageway, in which case the source is preferably in a form which resists undesirable interaction e.g. dissolution, with the flowing liquid system. For instance, the radionuclide source e.g. $^{14}C$ or $^{147}Pm$, may be contained within a suitable enclosure such as a thin-walled metal tube. Also, for instance, radionuclide sources e.g. $^{63}Ni$, may be plated with a suitable metal plating such as gold or silver or may be covered with a suitable polymeric coating to protect the source against undesirable interaction with the liquid system.

Alternatively the radionuclide source may be located outside, though adjacent to, the liquid passageway, and such location of the source advantageously avoids problems of undesirable interaction of the source with the flowing liquid system. Preferred external radionuclide sources comprise gamma-emitting radionuclides such as $^{57}Co$ or $^{241}Am$ and Bremsstrahlung sources such as $^{147}Pm$ and $^{3}H$.

It will be appreciated that the geometrical arrangement of the detector may be varied with a view to maximising the fluorescence which is produced and monitored. Suitable variations and arrangements of detector will be apparent to workers in the art. In particular, however, optical filters may be employed between the sample and the fluorescence monitor to select particular wavelengths for monitoring; for example, to filter out background fluorescence such that fluorescence due to the species which is being determined is preferentially monitored.

Generally also substances may be added to the liquid medium to increase the total fluorescence including that of the species it is desired to determine, though this typically also increases the background fluorescence of the solvent. Such added substances are generally fluorescent substances and may be the same as or similar to those which are used as fluorescent dope materials for quenching measurements e.g. substances such as toluene and p-xylene. Such added fluorescent substances may be used in conjunction with optical filters as described above.

Any suitable form of fluorescent monitoring may be used to detect the fluorescence produced, though preferably the monitor comprises a photomultiplier or similar device. Conveniently the transparent liquid passageway and fluorescence monitor e.g. photomultiplier, are contained in appropriate arrangement in a suitable light tight enclosure such that the photomultiplier "sees" only the radiation due to fluorescence of the species and advantageously substantially the total amount of this fluorescence is monitored. The photomultiplier monitor may be coupled to a suitable counting instrument, such as a scaler counter, and the photomultiplier and counter may be adjusted having regard to the expected level of fluorescence. The quantity of the fluorescent or quenching species present in the liquid may be determined in the normal manner from the fluorescence produced or quenched.

The invention also includes flow cells for use in fluorimetric detectors adapted for use with flowing liquid systems. Such flow cells typically comprise a passageway for liquid flow and a radionuclide source for excitation of fluorescence, in which the walls of the passageway are transparent at least in part.

The detector of the invention may be used in liquid chromatography systems in general, including in particular HPLC system, and thus the invention further includes liquid chromatography systems which comprise a fluorescence detector according to the invention. Such systems may be adapted for normal phase reverse phase and other chromatographic uses, e.g. ion-exchange chromatography, for detection of both fluorescent species and species which cause quenching of fluorescence.

The detector and method of the present invention permit the detection and determination of fluorescent species in liquid systems, in particular flowing liquid systems, including especially liquid chromatography systems, in a manner which advantageously avoids the instability problems which are a feature of previous visible radiation excitation fluorescence detectors.

The invention is further described by way of illustration only in the following examples the first of which relates to a $^{63}Ni$ beta-induced fluorescence (BIF) liquid chromatography system, the examples referring to the accompanying diagrams in which:

FIG. 9 is a schematic representation of a BIF detector incorporating the flow cell of FIG. 8;

EXAMPLE 1

Figure 1:
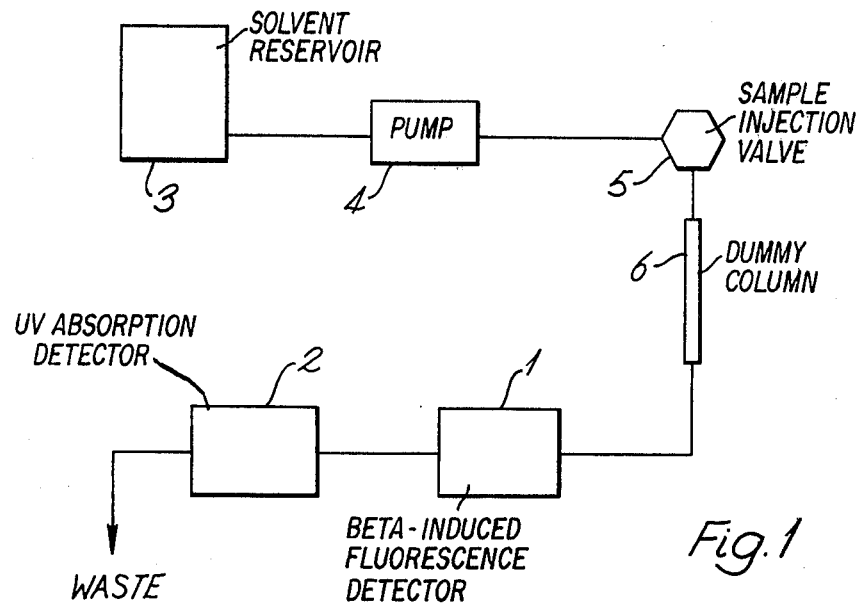
FIG. 1 is a schematic representation of the apparatus used in Example 1 for testing of the $^{63}Ni$ BIF detector.

With reference to FIG. 1, the performance of a beta-induced fluorescence detector accoring to the invention 1 is compared with that of a conventional UV absorption detector 2 in a liquid chromatography system. Solvent (hexane and methanol—HPLC grade, Fisons Scientific Apparatus Limited, or toluene—A.R. grade, BDH Chemicals Limited) is pumped from a solvent reservoir 3 by means of a conventional reciprocating pumping system 4 (supplied by Anachem Limited) at a constant flow rate of about 1 ml. $min^{-1}$. Samples are introduced into the solvent flow by means of an Altex model 905 sample injection valve 5 fitted with a 20 $\mu l$ sample loop. The solvent-sample flow is passed from the sample injection system 5 to a 25 centimeter length of empty stainless steel tubing (i.d. 0.03 ins.) 6 which acts as a dummy column spreading out the samples and producing a more realistic peak shape than would be obtained if the sample injection valve 5 was connected directly to the detectors 1 and 2. The eluant from this column 6 is passed into the beta-induced fluorescence detector 1.

Figure 2:
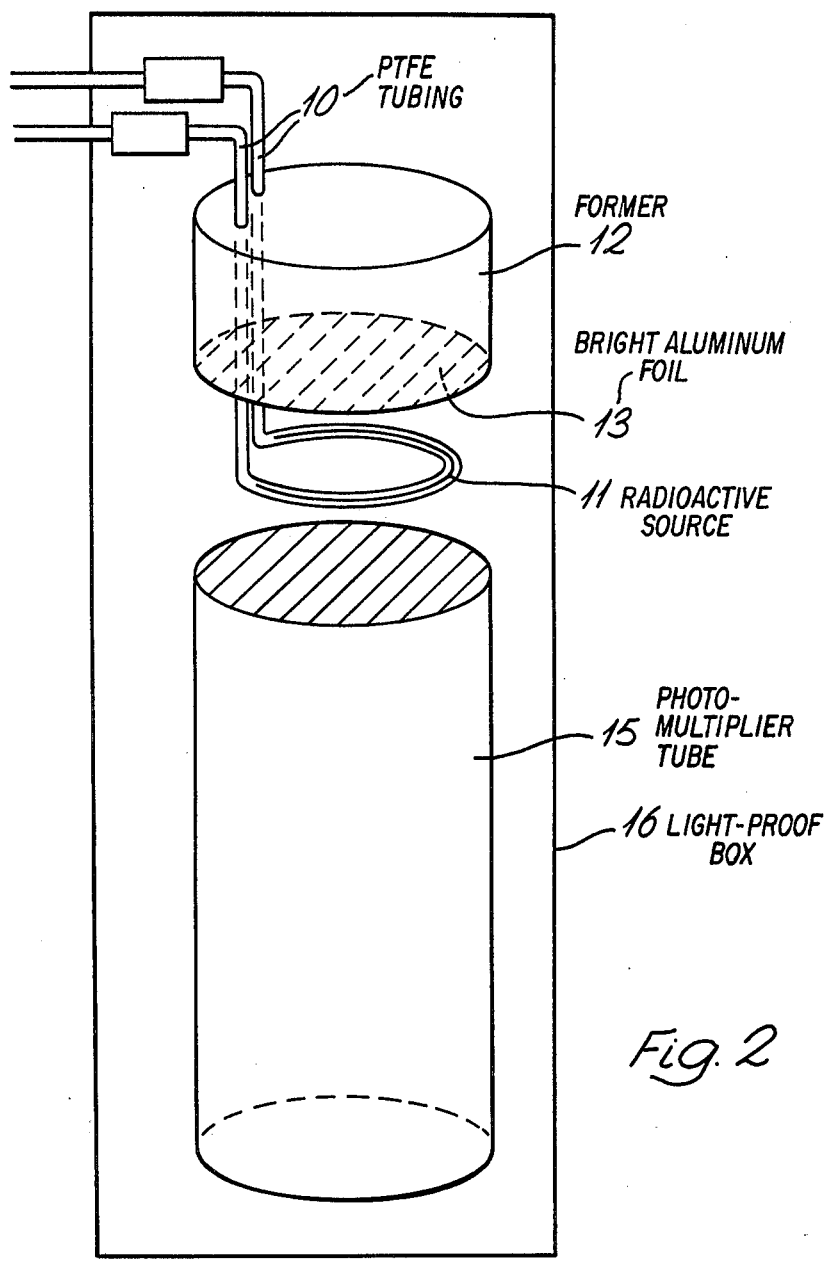
FIG. 2 is a detailed representation in enlarged scale of the $^{63}Ni$ beta induced fluorescence detector of FIG. 1.

With reference to FIG. 2, the flow cell of the beta-induced fluorescence detector 1 consists of a length of PTFE tubing 10 (i.d. 0.075 cm) which contains a 5 centimeter length of 0.05 cm diameter wire 11 on to which 15 mCi of $^{63}Ni$ has been electrodeposited. The PTFE tubing 10 is formed into an almost complete single loop with a diameter of approximately 2 cm. The shape of the loop is maintained by recessing the PTFE tubing into a former 12 covered with bright aluminium foil 13 to act as a reflector. The flow cell 10 containing the radioactive source 11 is viewed from below by a photomultiplier tube 15, the whole being enclosed in a light proof box 16. The $\beta-$ decay of the $^{63}Ni$ source 11 excites fluorescence from materials passing through the flow cell 10 and the detected fluorescence is counted on a SR5 scaler-rate meter (Nuclear Enterprises Limited), with the count rate being continuously monitored on a chart recorder.

The photomultiplier tube 15 used is an EMI type S9514, with a soda-glass end window adjacent the flow cell 10. For this reason only materials with a florescent emission of $\lambda > 370$ nm are detected. On the other hand the use of a soda-glass PMT permits use of ordinary HPLC grade solvent without the problem of an inconveniently high background from solvent fluorescence.

After passing through the beta-induced-fluorescence detector flow cell 10 the eluant is then monitored for UV absorption (254 nm) using an Altex model 150 biochemical monitor 2. The use of a conventional detector 2 enables a cross-check to be made of the quantity of sample injected and provides a monitor for ensuring that material is not retarded by adsorption on the wire 11 in the BIF flow-cell.

Low concentration solutions of anthracene, naphthalene, 2,5-diphenyloxazole (POP), 1,4-di-(2-(5-phenyloxazolyl)) benzene. (POPOP), benzoquinone and 9-aminoacridine are prepared and injected into appropriate flowing solvents. As pure solvent flows through the system counts are registered at a reasonably constant rate, typically at about $6 \times 10^4$ $min^{-1}$ with hexane as solvent. When samples of the above materials pass through the flow cell 10 the count rate increases to a maximum and then returns to the level characteristic of the pure solvent, and thus the recorder trace shows a peak of the kind generally associated with liquid chromatograph detectors.

The operating conditions of the detection electronics are optimised in the usual way, by seeking the maximum value of $(S-B)^2/B$, where S=count rate with the solvent plus fluorescent solute flowing through the cell, and B=count rate for the solvent alone.

Figure 3:
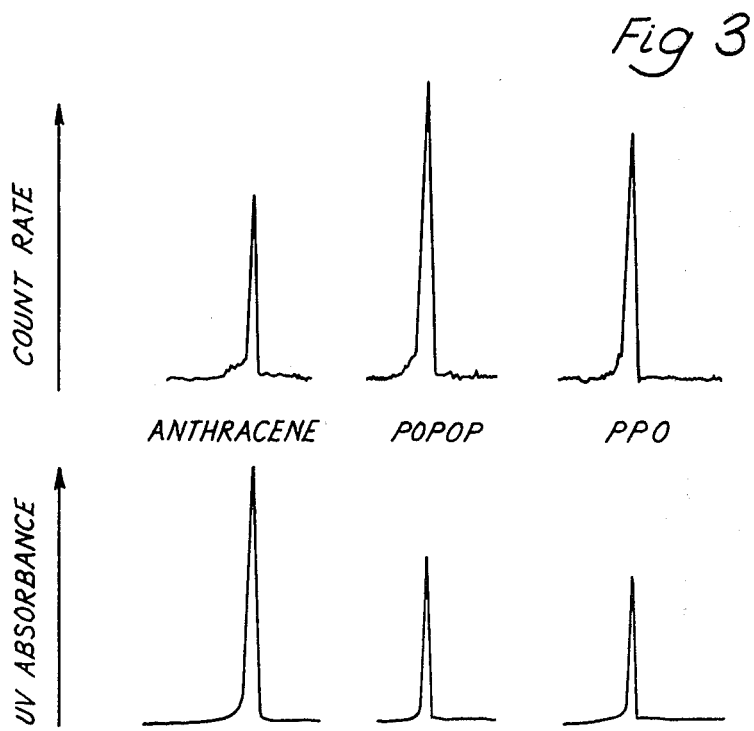
FIG. 3 is a graph showing count rate variations recorded from the BIF detector of FIG. 1 for a number of samples in a flowing hexane system compared with UV absorption records for the same samples.

Using the dummy column 6, as described above, 20 $\mu l$ samples of dilute solutions of the fluorescent materials are passed through the apparatus and the UV absorption traces obtained are similar to those that would be produced following reasonable chromatographic separations. The count rate variations recorded from the BIF detector 1 for a number of samples in hexane is shown in FIG. 3 which also includes the UV absorption records for the same samples. The similarity in peak shape strongly suggests that the BIF detector 1 responds to the instantaneous concentration of fluorescent material within the flow cell. No tailing is observed and the count rate in pure solvent after a peak returned cleanly to the value before the peak.

For all samples passed through the flow cell 10 a "fluorescent count" is obtained by noting the integrated count under each peak and correcting for the equivalent count obtained in the same time interval with pure solvent along passing through the cell. The fluorescent counts obtained from a number of dilute solutions eluted with hexane are shown below in Table 1, the results being means of several experiments and the errors being standard errors.

TABLE 1

| Fluorescence count from dilute solutions eluted in hexane | | |
|---|---|---|
| Solute | Concentration | Count from 20 ng sample |
| Anthracene | 1 $\mu g$ $ml^{-1}$ | 1520 ± 120 |
| Benzoquinone | 1 | 1110 ± 100 |
| Naphthalene | 1 | 1350 ± 150 |
| POPOP | 1 | 7710 ± 200 |
| PPO | 1 | 5080 ± 150 |

Figure 4:
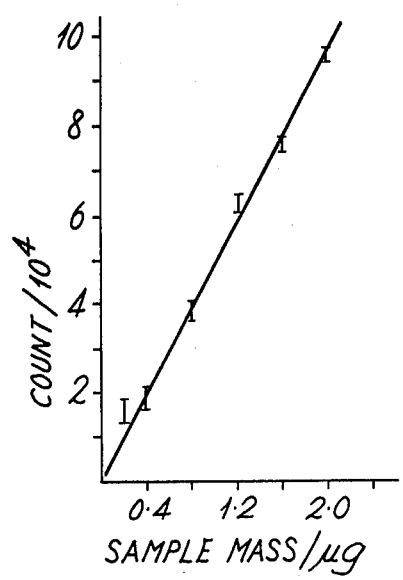
FIG. 4 is a graph of count for the BIF detector of FIG. 1 against sample mass for 9-amino acridine in the range 10-100 μg ml$^{-1}$.
Figure 5:
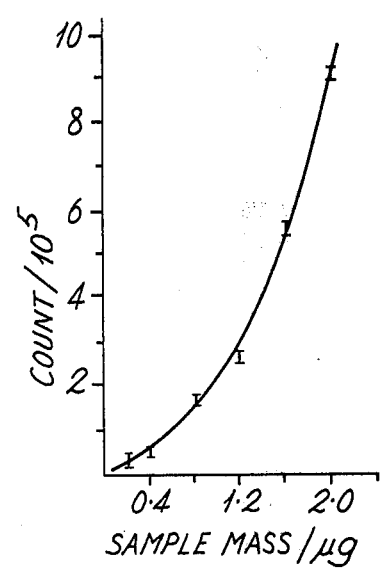
FIG. 5 is a similar graph for anthracene.
Figure 6:
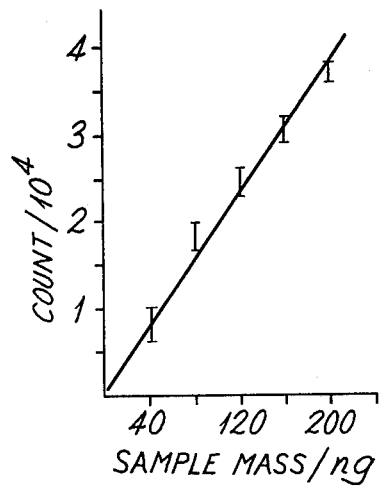
FIG. 6 is a further similar graph for anthracene though in the sample mass range 1-10 μg ml$^{-1}$.

The fluorescent count from solutions is also determined over a range of concentrations. The results for 9-amino acridine eluted in methanol are given in FIG. 4, where the horizontal axis shows the mass of compound contained in the 20 $\mu l$ sample. Clearly the detector response is linear over the range of concentrations studied (10–100 $\mu g$ $ml^{-1}$). Results for anthracene eluted with toluene are shown in FIG. 6. Again the detector response is linear over the concentration range shown in the figure (1–10 $\mu g$ $ml^{-1}$). However results obtained at higher concentrations of anthracene show an apparent deviation from linearity, though it is believed that this arose as an artefact of the counting electronics used and it was subsequently found that the response was in fact linear over this concentration range. The anthracene results are shown in FIG. 5 for the same concentration as the 9-amino acridine results of FIG. 4 (10–100 µg ml$^{-1}$).

EXAMPLE 2

An alternative form of BIF detector was constructed using a $^{147}$Pm beta-emitting source, and was tested as a BIF (beta-induced fluorescence) and QBIF (quenched beta-induced fluorescence) detector in chromatographic applications.

Figure 7:
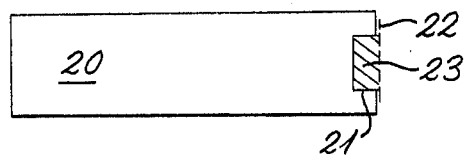
FIG. 7 is a diagrammatic representation in enlarged scale of a $^{147}Pm$ source as used in the BIF detector of Example 2.
Figure 8A:
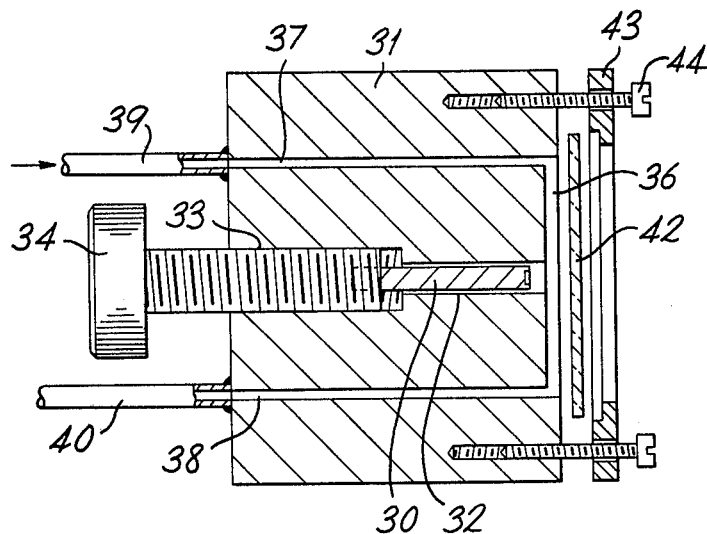
FIGS. 8a and 8b are diagrammatic representations of two views, a vertical axial section and an end elevation, of the BIF detector flow cell as used in Example 2, incorporating the $^{147}Pm$ source of FIG. 7.
Figure 8B:
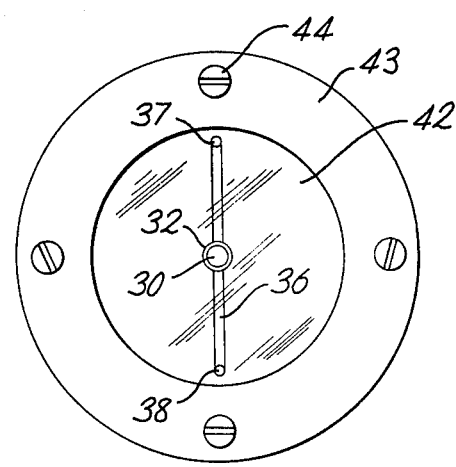

The source used was a 1 mCi "point source" of promethium—147 ($t_{\frac{1}{2}} \sim 2.6$ years, $E_{max} \sim 225$ keV), supplied by the Radiochemical Centre, Amersham, code PHC. 32. With reference to FIG. 7, the source takes the form of a 10×2 mm (diameter) stainless steel rod 20 having a 1×1 mm (diameter) recess 21 machined into one end thereof, the mouth of the recess being closed by a fixed 5 µm thick rolled silver foil disc, retaining the $^{147}$Pm activity 23 as carbonate within the recess. With reference to FIG. 8 the source 30 is mounted in a flow cell comprising a cylindrical stainless steel body 31 having drilled through it along its axis a bore hole, which has a section 32 of relatively small diameter towards the front face of the cell to fit closely around the source 30 and which towards the rear of the cell increases diameter by way of a step into an internally threaded section 33 for accommodating a source-positioning screw 34 to which the source 30 is attached. The front face of the steel body 31 has a groove 36 machined into it symmetrically along part of a diameter, the extremities of the groove 36 communicating by way of passageways 37 and 38 drilled through the body 31 with inlet 39 and outlet 40 tubes which are braised into the rear face of the cell. The front face of the cell is polished to provide a leak-proof seal with a 2×19 mm (diameter) spectrosil A window 42 when this is held in place by a retaining ring 43 and four bolts 44. In use the active volume of the cell may be varied between 1.5 and 10 µl by adjustment of the source-positioning screw 34.

This cell design was easy to fabricate and made use of a commercially available $^{147}$Pm source, but was not intended as an optimum or ideal design.

With reference to FIG. 9, the flow cell 50 described above is incorporated into a BIF detector system, the flow cell and photo-multiplier tube (EMI type 9804 QB, 13 stage, quartz window) being enclosed in a light-tight box with their windows adjacent one another with an air gap of about 1 mm between them. The electronic units of the fast counting system were NIM modules supplied by Canberra Ltd. and comprised a Model 2110 timing filter amplifier 52, a Model 1433 discriminator 53, a Model 1776 dual scaler 54, a Model 3102 high voltage supply 55 and a Model 2081 fast ratemeter 56. Signals from the detection system are recorded on a chart recorder 57 connected to the ratemeter 56, and quantified by noting the integrated count registered on the scaler 54.

The inlet to the flow cell 50 is connected to the column 58 of a conventional HPLC system fed by a conventional reciprocating pump.

The BIF detector as described above was tested using both normal phase and reverse phase chromatography. Normal phase chromatography was carried out using an Altex 15 cm column packed with 5 µm Lichrosorb eluted with hexane (Fisons Ltd. HPLC grade) acetonitrile or toluene (Fisons, HPLC grade) as polar modifiers. Reverse phase chromatography was carried out using a 25 cm column packed with 10 µm Spherisorb ODS eluted with methanol or acetonitrile (Fisons, HPLC grades) and distilled water. The few occasions when other eluants were used will be referred to specifically. Samples were loaded on the columns using an Altex Model 902 sample injection valve fitted with a 20 µl injection loop.

BIF in Normal Phase HPLC

Solutions of a variety of materials in hexane were passed through the chromatograph system described above, and the count rates were determined and compared with the count rate for the pure solvent. Samples of diphenyloxazole, dibenzofuran and bis methyl-styryl-benzene in toluene and also the latter compound in a hexane/toluene mixture were also passed through the chromatograph and similarly monitored. In the cases when toluene and hexane/toluene solutions were used as eluants, a pyrex window was used in front of the photo-multiplier tube. The results obtained are given in Table 2 below, also indicating background counts for the solvents alone.

TABLE 2

Response of BIF detector to eluted materials (normal phase chromatography)

| Compound | Eluting solvent | Fluorescent background cps | Response (counts/µg of sample) |
|---|---|---|---|
| p-terphenyl | Hexane | 12,000 | 813,600 |
| anthracene | " | " | 287,000 |
| fluorene | " | " | 263,000 |
| 1,6-diphenyl-1,3,5-hexatriene | " | " | 520,000 |
| 1,4-di-(2-methyl-styryl)benzene | " | " | 517,200 |
| biphenyl | " | " | 50,300 |
| tetraphenyl-butadiene | " | " | 251,600 |
| naphthalene | " | " | 105,300 |
| phenanthrene | " | " | 45,000 |
| acenaphthene | " | " | 153,700 |
| anisole | " | " | 38,100 |
| indene | " | " | 4,550 |
| benzo(a)pyrene | " | " | 338,100 |
| 3-methylcholanthrene | " | " | 191,800 |
| fluoranthene | " | " | 114,600 |
| diphenyl oxazole | Toluene | 180,000 | 8,726,800[a] |
| dibenzo furan | " | " | 759,600[a] |
| 1,4-di-(2-methyl-styryl)benzene | " | " | 5,353,500[a] |
| 1,4-di-(2-methyl-styryl)benzene | 99% Hexane / 1% Toluene | 25,200 | 1,903,000[a] |

Note
[a]Pyrex window in front of PMT

In all cases the eluting solvent was degassed by passing argon through it prior to use, though small negative peaks were noted on sample runs due to oxygen present in the samples.

Figure 10:
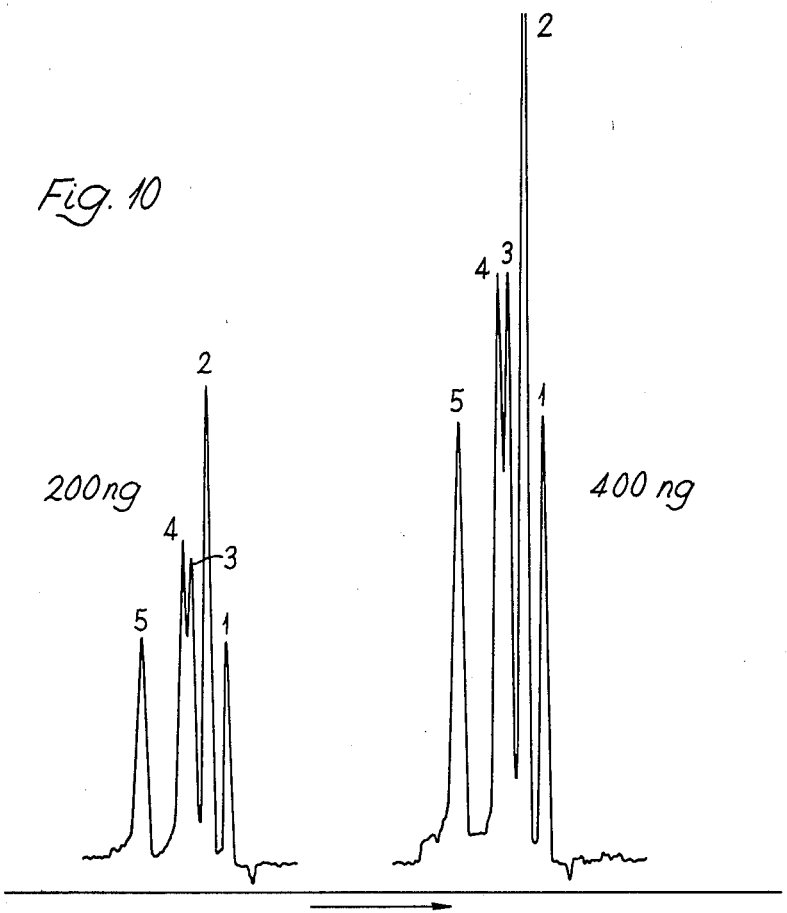
FIG. 10 is a graph showing response of the BIF detector of FIG. 9 to elution of normal phase chromatographically separated mixtures of five components at two concentrations.

With reference to FIG. 10, a typical chromatographic separation was carried out on a mixture of five compounds [(1)anthracene, (2)p-terphenyl, (3)perylene, (4)1,4-di-(2-methylstyryl) benzene and (5)1,6-diphenyl-1,3,5-hexatriene] for column loading of each component of 200 ng and 400 ng.

Figure 11:
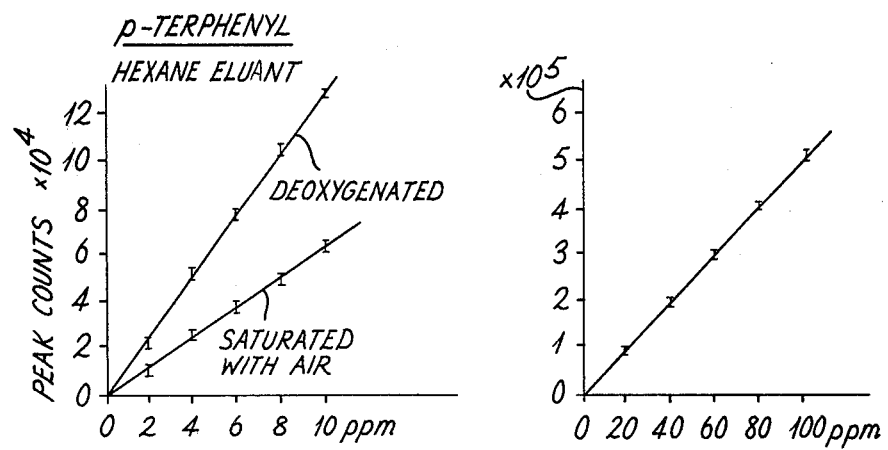
FIG. 11 are graphs of linearity curves of count against sample mass for p-terphenyl using the detector of FIG. 9.
Figure 12:
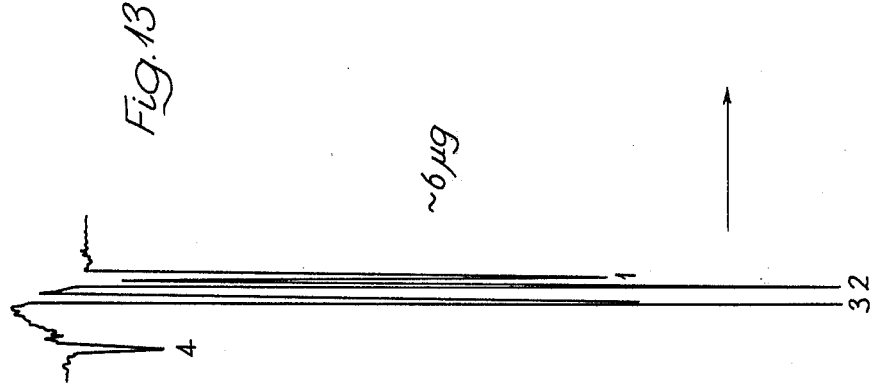
FIG. 12 is a similar graph for fluorene.

The linearity of response of the BIF detector to samples of varying concentrations was also determined for p-terphenyl and fluorene, and the results obtained are given in FIGS. 11 and 12 respectively. These Figures show that the response of the BIF detector was linear to within experimental error over a wide concentration range. The lower line in the 0–10 ppm graph of FIG. 7 relates to a sample in which the eluant was not degassed but was saturated with air, and shows that, although the detector response is lower when oxygen is present, it is still linear. All other determinations were carried out using deoxygenated eluants.

BIF in Reverse Phase HPLC

Solutions of a variety of materials in methanol were made up and passed through the chromatograph in the reverse phase chromatography mode. The results obtained are given in Table 3 below which is in a similar format to Table 2. Eluants were chosen with a view to causing elution approximately 1-2 minutes beyond the solvent edge. A pyrex glass filter was used between the flow cell and photomultiplier tube in all cases.

TABLE 3
Response of BIF detector to eluted materials (reverse phase chromatography)

| Compound | Eluting solvent | fluorescent background cps | Response,[a] (counts/μg sample) |
|---|---|---|---|
| Anthranilic acid | 77% methanol | 5,500 | 33,400 |
| Carbazole | 15% water | " | 35,000 |
| Indole | 8% toluene | " | 25,800 |
| Salicylic acid | | " | 39,000 |
| Anthranilic acid | 78% Acetonitrile | 14,700 | 69,000 |
| Carbazole | 14% water | | 111,400 |
| Indole | 8% p-Xylene | | 48,800 |
| 9-amino acridine | methanol | 2,000 | 9,000 |
| 1-Naphthol | 90% methanol 10% toluene | 8,000 | 63,000 |
| 1-Naphthol | 90% methanol 10% benzyl-alcohol | 5,500 | 25,300 |

[a] all responses obtained with pyrex window in front of PMT

Quenched BIF in Normal Phase HPLC

Figure 13:
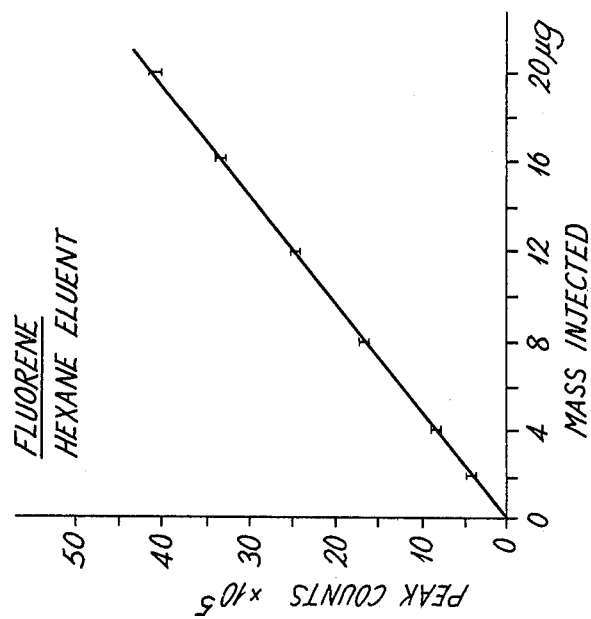
FIG. 13 is a graph showing quenching response of the BIF detector of FIG. 9 to elution of normal phase chromatographically-separated mixtures of four components at two concentrations.

The BIF detector was also used for detection of a wide range of compounds which cause quenching of fluorescence, the effect being seen as a dramatic drop in count rate as the quenching material passes through the BIF cell. The results obtained from a typical chromatographic separation of a mixture of four compounds [(1) hexane, (2) benzaldehyde, (3) anisaldehyde, and (4) propanone] are given in FIG. 13, the hump in the base line being due to an accidental elution of a trace fluorescent material.

Solutions of a variety of materials in hexane were made up and passed through the chromatograph, and the results obtained are given below in Table 4, the response given in terms of the counts lost from the eluent fluorescence.

TABLE 4
Response in QBIF mode of eluted materials (normal phase chromatography)

| Compound | Eluting Solvent | fluorescent background (cps) | Response, (−counts/μg sample) |
|---|---|---|---|
| 1,2-dibromoethene | hexane | 12,000 | 6,740 |
| iodoethane | " | " | 2,660 |
| 1-bromopropane | " | " | 2,130 |
| tetrachloroethene | " | " | 6,800 |
| 1,2-dichloroethane | " | " | 1,660 |
| nitrobenzene | " | " | 116,700 |
| chlorobenzene | " | " | 7,400 |
| p-dichlorobenzene | " | " | 7,700 |
| hexachlorbenzene | " | " | 7,650 |
| 3-chlorotoluene | " | " | 8,060 |
| 4-chlorotoluene | " | " | 6,600 |
| thiophen | " | " | 5,050 |
| propanone | 5% acetonitrile | 354,000 | 84,800 |
| butan-2-one | 95% toluene | " | 67,500 |
| ethanol | " | " | 119,400 |
| anisaldehyde | " | " | 182,600 |
| cinnamaldehyde | " | " | 268,400 |
| benzaldehyde | Toluene | 428,000 | 268,700 |
| nitropropane | " | " | 167,200 |
| nitrobenzene | 90% hexane 10% toluene | 350,000 | 235,400 |

Figure 14:
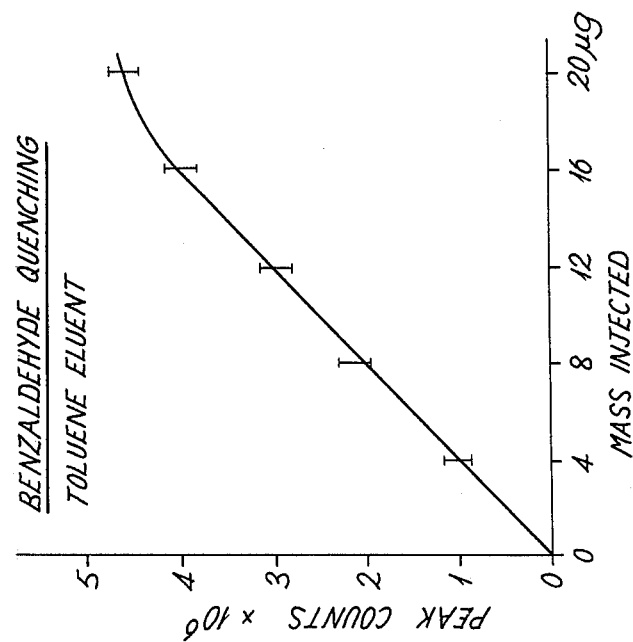
FIG. 14 is a graph of a linearity curve for benzaldehyde quenching using the detector of FIG. 9.

The linearity of response of the QBIF (quenched BIF) signal was determined against variation in the amounts of benzaldehyde and the results obtained are given in FIG. 14. It is believed that the apparent departure from linearity at high sample loadings (~20 μg) is an artefact of the counting electronics, and in any event the response is clearly linear at lower loadings.

Enhancement of Sensitivity

The effect of incorporating materials in the eluent which increase fluorescence was investigated for the reverse phase chromatographic detection of 1-naphthol in methanol and the normal phase chromatographic detection of 1,4-di-(2-methylstyryl)benzene in hexane. Toluene was used as the flurorecence increasing additive in both cases. The results obtained are given in Table 5 below, the anomalously low responses for bis methyl styrylbenzene at the 5% and 10% toluene addition apparently arising from a deficiency in the counting system used.

TABLE 5
Effect of adding fluorescent material to eluting solvents

| Compound | Eluting solvent | background fluorescent (cps) | Response (counts/μg sample) |
|---|---|---|---|
| 1 Naphthol | methanol | 2.000 | ~0 |
| " | 99% MeOH, 1% toluene | 3,050 | 6,900 |
| " | 95% MeOH, 5% toluene | 5,000 | 33,360 |
| " | 90% MeOH, 10% toluene | 8,000 | 63,640 |
| 1,4-di-(2-methylstyryl)benzene | hexane | 12,000 | 517,200 |
| 1,4-di-(2-methylstyryl)benzene | 99% hexane, 1% toluene | 36,500 | 1,927,400 |
| 1,4-di-(2-methylstyryl)benzene | 95% hexane, 5% toluene | 600,000 | 1,421,600 |
| 1,4-di-(2-methylstyryl)benzene | 90% hexane, 10% toluene | 650,000 | 1,466,500 |

Similarly the use of optical filters to filter out the solvent fluorescence was investigated. A pyrex glass slide was used as a crude filter, and also a L39 optical filter (cut off wavelength ~370 nm) was also used. A dramatic decrease in background fluorescence is achieved using the L39 optical filter as evidenced by the results given below in Table 6. The anomalously low response for 1,4-di-(2-methylstyryl)benzene at the 5% and 10% toluene addition levels is believed to be due to a deficiency of the counting electronics, counts being lost at high count rate.

TABLE 6

Effect of filtering fluorescence on response of BIF detector

| Compound | Eluting solvent | filter | background fluorescence cps | Response (counts/μg sample) |
|---|---|---|---|---|
| 1,4-di-(2-methylstyryl)benzene[b] | 99% hexane | — | 36,500 | 1,927,400 |
|  | 1% toluene | pyrex | 25,200 | 1,903,000 |
|  |  | L39 | 3,050 | 2,360,100 |
| " | 95% hexane | — | 600,000 | 1,421,620 |
|  | 5% toluene | L39 | 3,800 | 4,017,200 |
| " | 90% hexane | — | 650,000 | 1,466,500 |
|  | 10% toluene |  | 4,200 | 4,896,900 |
| Anthranilic acid[c] | 87% acetonitrile | pyrex | 16,200 | 69,800 |
|  | 5% H$_2$O | L39 | 2,250 | 70,700 |
|  | 8% p-xylene |  |  |  |

Notes
[b] normal phase chromatography
[c] reverse phase chromatography

Figure 15:
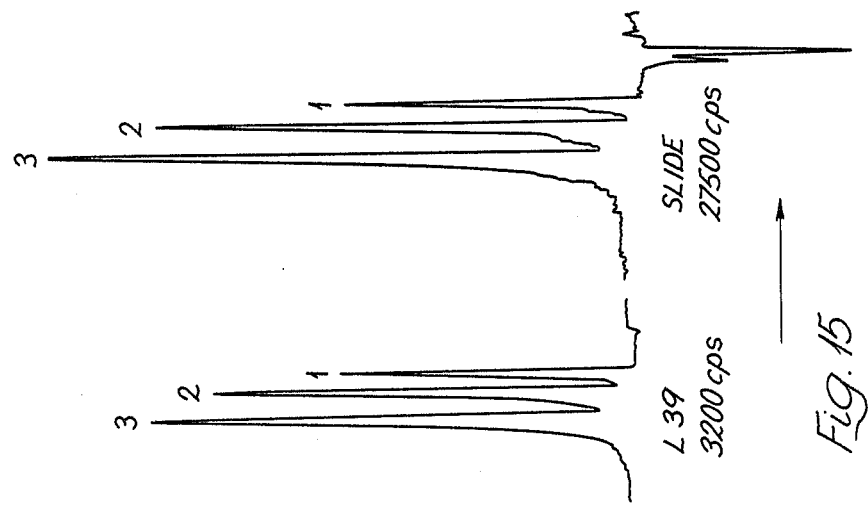
FIG. 15 is a graph showing response of the BIF detector of FIG. 9 to elution of a mixture of three components using two different optical filters.

Chromatograms were determined for mixtures containing 0.3 μg of each of three compounds [(1) fluoranthene, (2) benzo (a) pyrene, and (3) 3-methyl cholanthrene] with a 1% toluene in hexane eluting solvent using the pyrex slide and L39 optical filters. The results obtained are given in FIG. 15 showing an improvement in background "noise" following from the lowering of the background fluorescence count. Both chromatograms were obtained with the same instrument at the same setting, although the baseline of the L39 filtered chromatogram was adjusted to appear at the same level as the other signal. It may be noted that the L39 filter greatly reduces the negative-going sample-solvent peak, as this peak is due to the toluene fluorescence which is not detected when this filter is used.

The sensitivity of the BIF detector was investigated for detection of benzo (a) pyrene using the L39 optical filter and a 10% toluene in hexane mixture as eluting solvent. From the results obtained it was estimated that the detection limit was of the order of about 500 pg. Analogous results with other fluorescent materials indicated similar detection limits, though it is to be expected that the detection limits could be significantly improved if the nature of the radioactive source and design of flow cell were optimised.

We claim:

1. A method of detecting or determining a species contained in the flowing liquid eluant of a chromatographic separation, which comprises providing a $^{147}$Pm or $^{63}$Ni source of beta-particles, generating visible fluorescent radiation in the eluant by the action of the beta-particles thereon, causing the eluant to flow between the source of beta-particles and a light-sensitive detection means, so that flluorescent radiation generated in the eluant is detected, and a count rate thereof is measured, by the detection means, optically filtering said radiation to select particular wavelengths for detection by said detection means and monitoring the output of the detection means.

2. A method according to claim 1 wherein the concentration of the species to be detected or determined in the eluant is such that the fluorescent count, obtainable by integration from a plot of fluorescent count rate against time, is substantially linearly proportional to the amount of the species to be detected or determined.

3. A method according to claim 1 in which the eluant contains a species to be detected or determined which fluoresces when exposed to beta particles.

4. A method according to claim 1 in which the eluant contains a component which fluoresces when exposed to beta particles, and also contains a species to be detected or determined which quenches that fluorescence.

5. A method according to claim 1 in which the eluant is caused to flow through a cell of active volume between 1.5 and 10 microliters.

6. A fluorimetric detector for use in detecting or determining a species contained in the flowing liquid eluant of a chromatographic separation, comprising a $^{147}$Pm or $^{63}$Ni source of beta particles; a light-sensitive detection means, spaced from the source, for detecting visible fluorescent radiation generated in the eluant by the action thereon of beta-particles and for measuring a count rate of said fluorescent radiation; an optical filter between the liquid eluant and the detection means to select particular wavelengths for detection by said detection means and flow-causing means to cause the eluant to flow between the source and the detection means.

7. A fluorimetric detector according to claim 6 in which the flow-causing means comprises a flow cell between the source and the detector, the active volume of the flow cell being between 1.5 and 10 microliters.

8. A fluorimetric detector according to claim 6 in which the light-sensitive detection means is a photomultiplier.

9. A fluorimetric detector according to claim 6, further comprising recording means to monitor an electrical output signal from the detection means which is proportional to the count rate of the fluorescent radiation.

* * * * *